United States Patent [19]

Soubrier et al.

[11] Patent Number: 5,480,793
[45] Date of Patent: Jan. 2, 1996

[54] NUCLEIC ACID CODING FOR THE HUMAN ANGIOTENSIN CONVERTING ENZYME (ACE), AND ITS USES, ESPECIALLY FOR THE IN VITRO DIAGNOSIS OF ARTERIAL HYPERTENSION

[75] Inventors: Florent Soubrier; Francois Alhenc-Gelas, both of Paris; Christine Hubert, Sevres; Pierre Corvol, Paris, all of France

[73] Assignee: Institut National De La Sante Et De La Recherche Medicale, Paris, France

[21] Appl. No.: 288,709

[22] Filed: Aug. 12, 1994

Related U.S. Application Data

[62] Division of Ser. No. 460,126, May 23, 1990, 5,359,045.

[30] Foreign Application Priority Data

Sep. 27, 1988 [FR] France ................................. 88 12620

[51] Int. Cl.$^6$ ............................. C12N 9/48; C12N 15/63; C12N 1/21; C12N 15/57; C12P 21/02
[52] U.S. Cl. ..................... 435/212; 435/69.1; 435/320.1; 435/252.3; 536/23.2
[58] Field of Search ............................ 435/320.1, 252.3, 435/69.1, 212

[56] References Cited

U.S. PATENT DOCUMENTS 4,358,535   11/1982   Falkow et al. .............................. 435/5

OTHER PUBLICATIONS

K. E. Bernstein et al, "The Isolation of Angiotensin–converting Enzyme cDNA" The Journal of Biological Chemistry, 263, n. 23, Aug. 15, 1988, pp. 11021–11024.

H. G. Bull et al, "Purification of Angiotensin–converting Enzyme from Rabbit Lung and Human Plasma by Affinity Chromatography", The Journal of Biological Chemistry, 260, n. 5, Mar. 10, 1985, pp. 2963–1972.

T. Kreofsky et al, "Purification of Human Lung Angiotensin Converting Enzyme (ACE) and Production of Anti–Catalytic Monoclonal Antibodies MoAb", Federation Proceedings (US), 45, (6) (1986).

R. K. A. Allen et al, "Monoclonal Antibodies to Human Pulmonary Angiotensin–Converting Enzyme", Australian and new Zealand Journal of Medicine, Suppl. 2, 18, (3): 547 (1988).

Iwata et al, JP–A–61 186 399 (Fuji Pharmaceutical), Chemical Abstracts, 106, p. 470, No. 16946f (1987).

Danilov et al, "Monoclonal Antibody to Human Lung Angiotensin–Converting Enzyme", Biotechnol. Appl. Biochem. 9: 319–322 (1987), & Chemical Abstracts, 108, p. 266, No. 18303j (1988).

Hiroshi et al, "Pharmacological Comparison of Captopril and MK–422 by a New Method for Measuring Activity of Angiotension Converting Enzyme (ACE)", Chemical Abstracts, vol. 104, 1986, voir p. 7, resume No. 179632y & Jpn. Circ. J. 49: 1175–1179 (1985).

Deluca–Flaherty et al, "Hybridization and Partial cDNA Sequence Analyses of Bovine Lung Angiotensin I–Converting Enzyme", Int. J. Pept. Protein Res. 29: 678–684 (1987) (cited on p. 2 of this application), Chemical Abstrcts, 107, p. 169, No. 148356u (1987).

Bernstein et al, "Multiple Forms of Angiotensin–Converting Enzyme ACE Complementary DNA", Biological Abstracts/RMM, accession No. 36105199, & Laboratory Investigation *US) 60(1): 9A (1989).

Primary Examiner—Robert A. Wax
Assistant Examiner—Kawai Lau
Attorney, Agent, or Firm—Nixon & Vanderhye

[57] ABSTRACT

The invention relates to the cloning and sequencing of the nucleic acid coding for the human ACE as well as the determination of the peptide chain corresponding to the ACE and of active peptide fragments which derive from it.

Another subject of the invention is the utilization of the above-mentioned polypeptides for the implementation of in vitro diagnostic methods for hypertension and for the design of new inhibitors of the ACE.

The invention also relates to the utilization of the nucleotide probes of the invention for the in vitro screening of the polymorphisms of the gene coding for the ACE.

3 Claims, 13 Drawing Sheets

|             |   | L | D | P | G | L | Q | P | G | (D) | F | S | A | D | E | A | G |
|-------------|---|---|---|---|---|---|---|---|---|-----|---|---|---|---|---|---|---|
| HUMAN       |   | L | D | P | G | L | Q | P | G | (D) | F | S | A | D | E | A | G |
| RABBIT      | T | L | D | P | G | L | L | P | G | D   | F | A | A | D | N | A | G |
| BEEF CATTLE | E | L | D | P | A | L | Q | P | G | N   | F | P | A | D | E | A | G |
| PIG         |   | L | D | S | A | L | Q | P | G | C   | F | T | A | D | E | A | G |
| MOUSE       |   | L | D | P | G | L | Q | P | G | N   | F | S | P | D | E | A | G |

Fig. 1

| | | | |
|---|---|---|---|
| CN1 | 5.6 | L K Q G W T P R R | 882-890 |
| CN2 | 9.7 | G H I Q Y F | 962-967 |
| CN3 | 10.9 | P P E F W E G S | 310-317 |
| CN4 | 12.1 | A L E K I A F L P F G Y L V D Q - R - G V F | 429-450 |
| CN5 | 12.3 | V V P F P D K P N L D V T S T - L Q | 268-285 |
| CN6 | 12.8 | E T T Y S V A T V | 719-727 |
| CN7 | 13.0 | K L G F S R P W P E A | 1143-1153 |
| CN8a | 14.0 | L E(K) P T D G R E V V - H A | 917-930 |
| CN8b | - | W A(Q) S W E N I Y D | 257-266 |
| CN9 | 19.3 | A T S R K Y E D L L | 746-755 |
| CN10 | 20.6 | V G L D A L D A Q | 560-568 |
| CN11a | 22.2 | L F A W E G W H N A A G I P L K P L | 156-174 |
| CN11b | - | Y E T P S L - Q D L E R L | 800-812 |

Fig. 1A

```
                                                                GCCGAGCACCGCCACCGCGTC  22

ATGGGGCCGCCTCGGGCCGGGGCCGGGGCCGGGCCTGCTGCCGCTGCTGCTGCCGCTGCTGCTGCCG
MetGlyAlaAlaSerGlyArgArgGlyProGlyLeuLeuLeuProLeuLeuLeuProLeuLeuLeuPro
-29                                                          -20                              -10

CCGCAGCCCCGCCCTGGGCGTTGGACCCCGGCAGCCCGGCTGCAGCCCGGCAACTTTCTGCTGACGAGGCCGGG  157
ProGlnProAlaLeuAspProGlyLeuGlnProGlyAsnPheSerAlaAspGluAlaGly
                                                             +1                        10

GCGCAGCTCTTCGCGCAGAGCTACAACTCCAGCGCCGAACAGGTGCTGTTCCAGAGCCAGAGCCAGCCGCCAGC
AlaGlnLeuPheAlaGlnSerTyrAsnSerSerAlaGluGlnValLeuPheGlnSerValAlaAlaSer
         20                                      30

TGGGCCACGACACCAACATCACCGCGGAGAATGCAAGGCGCCAGGAGGAGCAGCCCTGCTCAGC  292
TrpAlaHisAspThrAsnIleThrAlaGluAsnAlaArgArgGlnGluGluAlaAlaLeuLeuSer
40                                     50                                     60

CAGGAGTTTGCGGAGGCCTGGGGCCAGAAGGCCAAGGAGCTGTATGAACCGATCTGGCAGAACTTCACG
GlnGluPheAlaGluAlaTrpGlyGlnLysAlaLysGluLeuTyrGluProIleTrpGlnAsnPheThr
                                        70                                      80

GACCCCGCAGCTGCGCAGGATCATCGGAGCTGTGCGAGCCCTGGCTCTGCCAACCTGCCCCCTGGCT  427
AspProGlnLeuArgArgIleIleGlyAlaValArgThrLeuGlySerAlaAsnLeuProLeuAla
                          90                                      100

AAGCGGCAGCAGTACACCGCCTGCTAAGCAACATGAGCAGGATCTACTTCACCGCCAAGGTCTGCCTC
LysArgGlnGlnTyrAsnGlnLeuSerAsnMetSerArgIleTyrSerThrAlaLysValCysLeu
                                          120

Fig. 3A
```

```
CCCAACAAGACTGCCACCTGCTGGTCCCTGGACCCAGATCTCACCAACATCCTCCTGGCTTCCTCGCGA 562
Pro Asn Lys Thr Ala Thr Cys Trp Ser Leu Asp Pro Asp Leu Thr Asn Ile Leu Leu Ala Ser Ser Arg
     130                              140                             150
AGCTACGCCACCATGCTCCTTGCCTGTTTGCCTTGGGAGGGCTGGCACAACGCTGCGGGCATCCCGCTGAAACCGCTG
Ser Tyr Ala Met Leu Leu Phe Ala Cys Leu Leu Gly Trp Glu Gly Trp His Asn Ala Ala Gly Ile Ile Pro Leu Lys Pro Leu
                 160                             170
TACGAGGATTCACTGCCCTCAGCAATGAAGCCTACAAGCAGGACGGCTTCACACACGGGGGCC 697
Tyr Glu Asp Phe Thr Ala Leu Ser Asn Glu Ala Tyr Lys Gln Asp Gly Phe Thr Asp Thr Gly Ala
                 180                             190
TACTGGCGCTCCTGGTACAACTCCCCCACCTTCGAGGACTGGAACACCTACCAACAGCTAGAG
Tyr Trp Arg Ser Trp Tyr Asn Ser Pro Thr Phe Glu Asp Leu Glu His Leu Tyr Gln Gln Leu Glu
                 200                             210
CCCCTCTACCTGAACCTCCATGCCTTTGTCCGCCGCCATCTGCTGGAGAGACAGATAC 832
Pro Leu Tyr Leu Asn Leu His Ala Phe Val Arg Arg Ala Leu His Arg Arg Tyr Gly Asp Arg Tyr
                 220                             230                             240
ATCAACCTCAGGGACCCATCCCTGCTCATCTGCTGGGAGACATGTGGCCCAGAGCTGGAAAACATC
Ile Asn Leu Arg Gly Pro Ile Pro Ala His Leu Leu Gly Asp Met Trp Ala Gln Ser Trp Glu Asn Ile
                 250                             260
TACGACATGGTGGTGCCTTTCCCAGACAAGCCCAACCTCGATGTCCAGTACTGCTGCAGCAG 967
Tyr Asp Met Val Val Pro Phe Pro Asp Lys Pro Asn Leu Asp Val Thr Ser Thr Met Leu Gln Gln
                 270                             280
```

Fig. 3B

```
GGCTGGAACGCCACGCACATGTTCCGGGTGGCAGAGGAGTTCTTCACCTCCCTGGAGCTCTCCCCATG
GlyTrpAsnAlaThrHisMetPheArgValAlaGluGluPhePheThrSerLeuGluLeuSerProMet
         290                                                    300

CCTCCCGAGTTCTGGGAAGGGTCGATGCTGGAGAAGCTGAAGCCCGACGGCGGGAAGTGGTGTGCCAC 1102
ProProGluPheTrpGluGlySerMetLeuGluLysProAlaAspGlyArgGluValValCysHis
310                         320                              330

GCCTCGGCTTGGGACTTCTACAACAGGAAAGACTTCAGGATCAAGCAGTGCACACGGGTCACGATGGAC
AlaSerAlaTrpAspPheTyrAsnArgLysAspPheArgIleLysGlnCysThrArgValThrMetAsp
                340                                           350

CAGCTCTCCACAGTGCACCATGAGATGGGCCATATACAGTACTACCTGCAGTACAAGGATCTGCCC 1237
GlnLeuSerThrValHisHisGluMetGlyHisIleGlnTyrTyrLeuGlnTyrLysAspLeuPro
        360                                   370

GTCTCCCTGCTCGGGGGGCCAACCCCCGGCTTCCATGAGGCCATTGGGACGTGCTGGCGCTCTCGGTC
ValSerLeuArgArgGlyAlaAsnProGlyPheHisGluAlaIleGlyAspValLeuAlaLeuSerVal
     380                                390

TCCACTCCTGAACATCTGCACCAAAAATCGGCTGCTGGACCGTGTCACCAATGACACGGAAAGTGAC 1372
SerThrProGluHisLeuHisLysIleGlyLeuLeuAspArgValThrAsnAspThrGluSerAsp
400                            410                           420

ATCAATTACTTGCTAAAAAATGGCACTGGAAAAAATTGCCTTCCTGCCCTTTGGCTACTTGGTGGACCAG
IleAsnTyrLeuLeuLysMetAlaLeuGluLysIleAlaPheLeuProPheGlyTyrLeuValAspGln
                430                               440
```

```
TGGCTGGGGGGTCTTTAGTGTGGGCCGTACCCCCCCTTCCCGCTACAACTTCGACTGGTGGTATCTT  1507
TrpArgTrpGlyValPheSerGlyArgThrProProSerArgTyrAsnPheAspTrpTrpTyrLeu
               450                          460
CGAACCAAGTATCAGGGGATCTGTCCTCCTGTTACCGAAACGAAACCCACTTTGATGCTGGAGCTAAG
ArgThrLysTyrGlnGlyIleCysProProValThrArgAsnGluThrHisPheAspAlaGlyAlaLys
           470                          480
TTTCATGTTCCAAATGTGACACCATACATCAGGTACTTTGTGAGTTTTGTCCTGCAGTTCCAGTTC  1642
PheHisValProAsnValThrProTyrIleArgTyrPheValSerPheValLeuGlnPheGlnPhe
             490                          500                      510
CATGAAGCCCTGTGCAAGGAGGCAGGCTATGAGGGCCACCAGTGTGACATCTACCGGTCCACC
HisGluAlaLeuCysLysLysGluAlaGlyTyrGluGlyProLeuHisGlnCysAspIleTyrArgSerThr
          510                          520                      530
AAGGCAGGGGCCAAGCTCCGGAAGGTGCTGCAGGCTCCTCCAGGCCCTGGCCAGGAGGTGCTG  1777
LysAlaGlyAlaLysLeuArgLysValLeuGlnAlaGlySerArgProTrpGlnGluValLeu
             540                          550
AAGGACATGGTCGGCTTAGATGCCCTGGATGCCCAGCCGCTGCTCAAGTACTTCCAGCCAGTCACCCAG
LysAspMetValGlyLeuAspAlaLeuAspAlaGlnProLeuLeuLysTyrPheGlnProValThrGln
          560                          570
TGGCTGCAGGAGCAGAACCAGCAGAACGGCGAGGTCCTGGGCTGGCCCGAGTACCAGTGGCACCCG  1912
TrpLeuGlnGluGlnAsnGlnGlnAsnGlyGluValLeuGlyTrpProGluTyrGlnTrpHisPro
580                          590                          600
```

```
CCGTTGCCTGACAACTACCCGGAGGGCATAGACCTGGTGACTGATGAGGCTGAGGCCAGCAAGTTTGTG
ProLeuProAspAsnTyrProGluGlyIleAspLeuValThrAspGluAlaGluAlaSerLysPheVal
         610                                620

GAGGAATATGACCGGACATCCCAGGTGGTGTGGAACGAGTATGCCGAGGCCAACTGGAACTACAAC   2047
GluGluTyrAspArgThrSerGlnValValTrpAsnGluTyrAlaGluAlaAsnTrpAsnTyrAsn
         630                                640

ACCAACATCACCACAGAGACCAGCAAGATTCTGCAGAAGAACATGCAAATAGCCAACCACACCCTG
ThrAsnIleThrThrGluThrSerLysIleLeuGlnLysAsnMetGlnIleAlaAsnHisThrLeu
         650                                660

AAGTACGGGACACCCAGGCCAGGAAGTTTGATGTGAACCAGTTGCAGAACACCACTATCAAGCGGATC    2182
LysTyrGlyThrGlnAlaArgLysPheAspValAsnGlnLeuGlnAsnThrThrIleLysArgIle
         670                                680                    690

ATAAAGAAGGTTCAGGACCTAGAACGGGAGCTGCCTGCCCAGGAGCTGGAGGAGTACAACAAGATC
IleLysLysValGlnAspLeuGluArgGluLeuProAlaGlnGluLeuGluGluTyrAsnLysIle
         700                                710

CTGTTGGATATGGAAACCACTACAGCGTGGCCACTGTGCCACCCGAATGGCAGCTGCCTGCAG     2317
LeuLeuAspMetGluThrThrTyrSerValAlaThrValCysHisProAsnGlySerCysLeuGln
         720                                730

CTCGAGCCAGATCTGACGAATGTGATGGCCACATCCCGGAAATATGAAGACCTGTTATGGGCATGGGAG
LeuGluProAspLeuThrAsnValMetAlaThrSerArgLysTyrGluAspLeuLeuTrpAlaTrpGlu
         740                                750
```

Fig. 3E

```
GGCTGGCCAGAGACAAGGCGGGGAGAGCCATCCTCCAGTTTTACCCGAAATACGTGGAACTCATCAAC 2452
Gly Trp Arg Asp Lys Ala Gly Arg Ala Ile Leu Gln Phe Tyr Pro Lys Tyr Val Glu Leu Ile Asn
760                          770                          780

CAGGCTGCCCGGCTCAATGGCTATGTAGATGCAGGGGACTCGTGGAGGTCTATGTACGAGAGACACCATCC 2587
Gln Ala Ala Arg Leu Asn Gly Tyr Val Asp Ala Gly Asp Ser Trp Arg Ser Met Tyr Glu Thr Pro Ser
    790                          800

CTGGAGCAAGACCTGGAGCGGCTCTTCCAGGAGCTGCAGCCACTCTACCTCAACCTGCATGCCTAC 2587
Leu Glu Gln Asp Leu Glu Arg Leu Phe Gln Glu Leu Gln Pro Leu Tyr Leu Asn Leu His Ala Tyr
        810                          820

GTGCGCCGGGCCCTGCACCGTCACTACGGGGCCCAGCACATCAACCTGGAGGGGCCCATTCCTGCTCAC 2722
Val Arg Arg Ala Leu His Arg His Tyr Gly Ala Gln His Ile Asn Leu Glu Gly Pro Ile Pro Ala His
            830                          840

CTGCTGGGGAACATGTGGGGCCAGACCTGGTCCAACATCTATGACTTGGTGCCCTTCCCTTCA 2722
Leu Leu Gly Asn Met Trp Ala Gln Thr Trp Ser Asn Ile Tyr Asp Leu Val Pro Phe Pro Ser
    850                          860                          870

GCCCCCTCGATGGACACCACAGAGGCTATGCTAAAGCAGGGCTGGACGCCCAGGAGGATGTTAAGGAG
Ala Pro Ser Met Asp Thr Thr Glu Ala Met Leu Lys Gln Gly Trp Thr Pro Arg Arg Met Phe Lys Glu
        880                          890

GCTGATGATTTCTTCACCTCCCTGGGGCTGCTCCCCGTGCCCCGTGCCTCCTGAGTTCTGGAACAAGTCGATG 2857
Ala Asp Asp Phe Phe Thr Ser Leu Gly Leu Leu Pro Val Pro Pro Glu Phe Trp Asn Lys Ser Met
            900                          910
```

Fig. 3F

```
CTGGAGAAGCCAACCGACGGGCGGGAGGTGGTCTGCCACGCCCTCGGCCTCGGGGACTTCTACAAGGGCAAG
Leu Glu Lys Pro Thr Asp Gly Arg Glu Val Val Cys His Ala Ser Ala Trp Asp Phe Tyr Asn Gly Lys
         920                              930

GACTTCCGGATCAAGCAGTGCACCACCGTGAACTTGGAGGACCTGGTGGCCCACCGAAATG   2992
Asp Phe Arg Ile Lys Gln Cys Thr Thr Val Asn Leu Glu Asp Leu Val Val Ala His Glu Met
         940                      950                      960

GGCCACATCCAGTATTTCATGCAGTACAAAGACTTACCTGTGGCCCTTGAGGGAGGGTGCCAACCCGGC
Gly His Ile Gln Tyr Phe Met Gln Tyr Lys Asp Leu Pro Val Ala Leu Arg Glu Gly Ala Asn Pro Gly
         970                      980

TTCCATGAGGGCCATTGGGGACGTGCTAGCCCTCTCAGTGTCTACGCCAAGCACCTGCACAGTCTC   3127
Phe His Glu Ala Ile Gly Asp Val Leu Ala Leu Ser Val Ser Thr Pro Lys His Leu His Ser Leu
                         990                      1000

AACCTGCTGAGTGAGGTGGCCAGCAGGCATGACGAGCATCAACTTTCTGATGAAGATGGCCCTTGAC
Asn Leu Leu Ser Glu Ser Glu Gly Gly Ser Asp Glu His Ile Asn Phe Leu Met Lys Met Ala Leu Asp
         1010                     1020

AAGATCGCCCTTTATCCCCTCAGCTACCTCGTCGATCAGTGGCGCTGGAGGTATTTGATGGAAGC   3262
Lys Ile Ala Phe Ile Pro Phe Ser Tyr Leu Val Asp Gln Trp Arg Trp Arg Val Phe Asp Gly Ser
         1030                     1040                     1050

ATCACCAAGGAGAACTATAACCAGGAGTGGTGGAGCCTCAGGCTGAAGTACCAGGGCCTCTGCCCCCCA
Ile Thr Lys Glu Asn Tyr Asn Gln Glu Trp Trp Ser Leu Arg Leu Lys Tyr Gln Gly Leu Cys Pro Pro
         1060                     1070
```

Fig. 3G

```
GTGCCCAGGACTCAAGGTGACTTTGACCCAGGGGCCAAGTTCCACATTCCTTCTAGCGTGCCTTAC 3397
Val Pro Arg Thr Gln Gly Asp Phe Asp Pro Gly Ala Lys Phe His Ile Pro Ser Ser Val Pro Tyr
                      1080                              1090

ATCAGGTACTTTGTCAGCTTCATCATCATCCAGTTCCAGTTCCAGAGGCCACTGCCAGGCAGCTGGCCAC 3532
Ile Arg Tyr Phe Val Ser Phe Ile Ile Gln Phe Gln Phe His Glu Ala Leu Cys Gln Ala Ala Gly His
            1100                              1110

ACGGGCCCCTGCACAAGTGTGACATCTACCAGTCCAAGGAGGCCGGGCAGCGCCCTGGCGAGGCCGACCGCC 3532
Thr Gly Pro Leu His Lys Cys Asp Ile Tyr Gln Ser Lys Glu Ala Gly Gln Arg Leu Ala Thr Ala
    1120                              1130                      1140

ATGAAGCTGGGCTTCAGTAGGCCGTGGCCGAAGCCATGCAGCTGATCACGGGCCAGCCAACATGAGC 3667
Met Lys Leu Gly Phe Ser Arg Pro Trp Pro Glu Ala Met Gln Ile Leu Ile Thr Gly Gln Pro Asn Met Ser
                  1150                              1160

GCCTCGGCCATGTTGAGCTACTTCAAGCCGCTGCTGGACTGGCTCCGGCACGGAGAACGAGCTGCAT 3667
Ala Ser Ala Met Leu Ser Tyr Phe Lys Pro Leu Leu Asp Trp Leu Arg Thr Glu Asn Glu Leu His
                      1170                              1180

GGGAGAAGCTGGGCCTGGCCGGCAGTACAACTCCGGCCGAACTCCGCTCGCTCAGAAGGGCCCCTCCCA
Gly Glu Lys Leu Gly Trp Pro Gln Tyr Asn Ser Ala Arg Ser Glu Gly Pro Leu Pro
              1190                              1200

GACAGCGGCCGCGTCAGTTCCGCGTCCTGGGACCTGGATGCCAGCAGGCCCGGTGGGCCAGTGG 3802
Asp Ser Gly Arg Val Ser Phe Leu Gly Leu Asp Leu Asp Ala Gln Ala Arg Val Gly Gln Trp
  1210                              1220
```

Fig. 3H

```
CTGCTGCTCTTCCTGGGCATCGCCCTGCTGGTAGCCACCCTGGGCCTTCAGCCAGCGGGCTCTTCAGCATC
LeuLeuLeuPheLeuGlyIleAlaLeuLeuValAlaThrLeuGlyLeu SerGlnArgLeuPheSerIle
                  1240                                  1250

CGCCACCGGCAGCCTCCAACCCGGCACTCCCACGGGCCCCAGTTCCGGCTTCCGGAGGTGGAGCTGAGACAC 3937
ArgHisArgSerLeuHisSerHisGlyProGlnPheGlySerGluValGluLeuArgHis
              1260                              1270

TCCTGAGGTGACCCGGCTGGGTCGGCCCCTGCCCAAGGGCCTCCCACCAGAGACTGGGATGGGAACACTG
Ser *
1277

GTGGGCAGCTGAGGGCGGT 4024
```

Fig. 3I

| | | | | | | | | | | | | |
|---|---|---|---|---|---|---|---|---|---|---|---|---|
| hACE  | T | V | H | H | E | M | G | H | 365 | E | A | I | 391 |
| hACE  | V | A | H | H | E | M | G | H | 963 | E | A | I | 989 |
| THERM | V | V | A | H | E | L | T | H | 146 | E | A | I | 168 |
| rNEP  | V | I | G | H | E | I | T | H | 581/588 | | | | |
| hCOLL | V | I | G | H | E | L | G | H | 222 | | | | |

| | | | | | | | | |
|---|---|---|---|---|---|---|---|---|
|       | H | L | H | K | - | I | - | G | 409 |
|       | H | L | H | S | - | L | - | N | 1007 |
| THERM | H | I | N | S | G | I | I | N | 238 |
| rNEP  | H | L | N | - | G | I | - | N | 635/643 |
| hCOLL | H | L | R | Y | R | I | E | N | 120 |

Fig. 4

NUCLEIC ACID CODING FOR THE HUMAN ANGIOTENSIN CONVERTING ENZYME (ACE), AND ITS USES, ESPECIALLY FOR THE IN VITRO DIAGNOSIS OF ARTERIAL HYPERTENSION

This is a divisional of application Ser. No. 07/460,126, filed May 23, 1990, 5,359,045.

The invention relates to a nucleic acid coding for the human angiotensin converting enzyme (ACE) as well as vectors containing this nucleic acid and the utilization of these latter for the production of human ACE. The invention also relates to the uses of this nucleic acid, especially in the area concerned with the design of new inhibitors of human ACE.

The ACE, or peptidyl dipeptidase A (EC 3.4.15.1), or also kininase II, plays an important role in the regulation of arterial blood pressure, by hydrolysing angiotensin I (inactive peptide released after cleavage of angiotensinogen by renin) to angiotensin II, a vasopressor agent playing a role in the mechanisms of arterial hypertension (SKEGGS, L. T., et al (1986) *J. Exp. Med.*, 103, 295–299).

The inhibition of the activity of the ACE by EDTA and metal chelators indicates that it is a metallopeptidase, more particularly a zinc peptidase capable of hydrolysing not only angiotension I but also brakykinin (a vasodilator and natriuretic peptide which it transforms into an inactive heptapeptide), and many other peptides with biological activity (YANG, H. Y. T. et al (1970) *Biochim. Biophys. Acta*, 214, 374–376; ERDOS, E. G., et al (1987) *Lab. Invest.*, 56, 345–348).

The ACE is a peptidase widely distributed in the organism, which is found, for example, in the form of a membrane enzyme at the surface of the vascular endothelial cells and renal epithelial cells, as well as in the form of an enzyme circulating in the plasma (ERDOS et al (1987) cited above; CARDWELL, P. R. B. et al (1976) *Science*, 191, 1050–1051; RYAN, U. S. et al (1976) *Tissue Cell*, 8, 125–145).

Methods for the purification of human or animal ACE have already been described (in particular in BULL H. G. et al (1985), *J. Biol. Chem.*, 260, 2963–2972; HOOPER, N. M. et al (1987), *Biochem. J.* 247, 85–93).

However, the structure of the human ACE is not known at present. Only some peptide sequences of the ACE of animal origin have been published (BERNSTEIN, K. E. et al (1988), *Kidney Int.*, 33, 652–655; HARRIS, R. B. et al (1985), *J. Biol. Chem.*, 260, 2208–2211; IWATA, K. et al (1982) *Biochem. Biophys. Res. Commun*, 107, 1097–1103; IWATA, K. et al (1983) *Arch. Biochem. Biophys.*, 227, 188–201; ST CLAIR, D. K. et al (1986) *Biochem. Biophys. Res. Commun*, 141., 968–972; SOFFER, R. L. et al (1987) *Clin. Exp. Hyp.* A9, 229–234).

Some attempts to clone the DNA coding for the animal ACE have been carried out starting from two organs rich in ACE, the kidneys and the lungs, but no complete nucleic acid coding for the animal ACE has, however, been described; only several fragments of such a nucleic acid have been described (DELUCA-FLAHERTY, C. et al (1987) *Int. J. Peptide Protein Res.*, 29, 678–684; BERNSTEIN K. E. et al, (1988, *J. Biol. Chem.*, 263, 11021–11024)). The quantities of messenger RNA (mRNA) coding for the ACE are probably too small in these organs to make possible the cloning of a complementary DNA (cDNA) of this mRNA. No attempt to clone the DNA coding for the human ACE has been described up to now.

Although the physiological role of the ACE in the extravascular tissues is still unknown, it is henceforth well established that this enzyme, which is found in the vascular endothelium and in the plasma, plays an essential role in the homeostasis of the circulation by its action of cleaving the carboxy-terminal dipeptide of angiotensin I, thus activating this latter by converting it into angiotensin II which is a vasoconstrictor peptide, which stimulates the production of aldosterone and facilitates adrenergic transmission.

In view of the essential role of angiotensin II in the control of arterial blood pressure, active research into the synthesis of inhibitors of the ACE has grown. Captopril was the first oral inhibitor of the ACE, followed by many other compounds. At present, the inhibitors of the ACE occupy an important place in the treatment of arterial hypertension. Since the complete structure of the ACE is not known, the above-mentioned inhibitors were designed on the basis of the structure of zinc proteases possessing enzymatic properties similar to those of the ACE, in particular on the basis of the structure of the active site of carboxypeptidase A (ONDETTI, M. A. et al (1977), *Science*, 196, 441–444).

Thus, in the absence of precise information concerning the structure of the ACE, and in particular regarding the active site(s) of the latter, it is easy to understand that the above-mentioned inhibitors of the ACE synthesized on the basis of analogies with the structure of other enzymes, may be molecules insufficiently active or not completely specific for the ACE and likely to possess an inadequate therapeutic action or to create undesirable side effects. Among such undesirable side effects may be distinguished in particular coughing fits, digestive disorders, skin rashes which may be associated with the inhibition of other enzymatic systems by the above-mentioned inhibitors of the ACE.

One of the aims of the present invention is to make possible the design of new inhibitors of the ACE which are more powerful and specific for the latter than are the current inhibitors mentioned above, which may possibly lead to a better efficacy at a lower dose and limit the risks of undesirable effects of such new inhibitors.

The subject of the present invention is the cloning and sequencing of the nucleic acid coding for the human ACE; this work was carried out starting from two banks of DNA complementary to the mRNA derived from endothelial cells of human umbilical veins and nucleotide probes deduced from peptide sequences obtained by sequencing purified fragments of the human ACE. The techniques used for the cloning and sequencing of the nucleic acid according to the invention will be more particularly described in the detailed description of the invention.

Reference will be made in what follows to the figures in which:

FIG. 1A shows the peptide fragments obtained from purified human ACE.

FIG. I presents the comparison of the amino-terminal amino acid sequences of the human ACE and of the ACEs obtained from rabbit, beef, pig and mouse;

FIG. 2 presents the respective positions of the nucleic acids of the three clones used for the determination of the nucleic acid coding for the human ACE;

FIGS. 3A-3I shows the nucleic acid, as well as the polypeptide deduced from this latter, corresponding to the human ACE;

FIG. 4 shows the homologies between certain peptide sequences of the human ACE (hACE), thermolysin (THERM), the neutral endopeptidase of the rat or rabbit (rNEP), and the collagenase of human skin fibroblasts (hCOLL).

Figure 2:
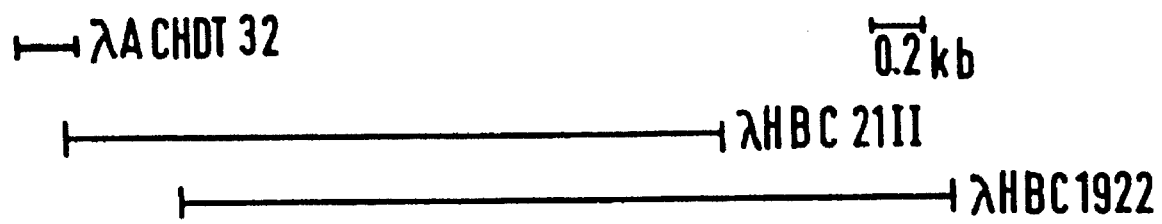

A more detailed study of the nucleic acid of the invention as well as of the polypeptide deduced from this latter and corresponding to the human ACE leads to the following observations:

the phase of the open reading frame of the nucleic acid of FIG. 3 is constituted by a DNA sequence defined by the nucleotides corresponding to the positions 23 and 109 of FIG. 1 coding for a signal peptide of 29 amino acids and a DNA sequence defined by the nucleotides situated at the positions 110 to 3940 of FIG. 3 and coding for a mature protein of 1277 amino acids;

the nucleic acid of the invention is characterized by a strong internal homology (higher than 60%) between the DNA sequence defined by the nucleotides situated at the positions 700 and 1770, and that defined by the nucleotides situated at the positions 2495 and 3565. The polypeptides of 257 amino acids coded respectively by the two DNA sequences mentioned above also show a strong homology between themselves (of the order of 67.7%). The strongest homology is located in the region of the amino acids of the central parts of the two polypeptides mentioned above; for example, the polypeptide defined by the amino acids situated at the positions 361 and 404, and that defined by the amino acids situated at the positions 951 and 1002, show a percentage homology of the order of 89%. The two homologous peptides each contains a His-Glu-Met-Gly-His sequence corresponding to the amino acids located at the positions 361 to 365 and 959 to 963 of FIG. 3. A comparative study (shown in FIG. 4) of this latter peptide sequence of 5 amino acids with the active sites of several enzymes, including thermolysin, suggests the fact that at least one of these two sequences of 5 amino acids which are found in the two homologous parts of the ACE may constitute a part of the active site of this latter;

the product of the above-mentioned open reading frame comprises 17 potential glycosylation sites, most of which are grouped in the N-terminal region of the molecule and in the region localized at the junction between the two domains of the above-mentioned homologous amino acids.

Hence, the present invention relates to any nucleic acid comprising the nucleotide sequence of FIG. 3 coding for the human ACE.

The invention relates more particularly to any nucleic acid comprising the DNA sequence defined by the nucleotides located at the positions 23 and 3940 of FIG. 3, and coding for the human pre-ACE of 1306 amino acids; the first 29 amino acids at the N-terminus represent the signal peptide and the remaining 1277 amino acids represent the mature human ACE.

The invention also relates to any nucleic acid comprising the DNA sequence defined by the nucleotides located at the positions 110 and 3940 of FIG. 3 and coding for the mature human ACE.

Another subject of the invention is any nucleic acid derived from the DNA sequence of FIG. 3 and coding for a polypeptide likely to possess enzymatic properties of the type of those of human ACE, in particular a polypeptide capable of hydrolysing angiotensin I and/or the kinins, in particular bradykinin, or any nucleic acid different from the one just mentioned with respect to its nucleotide sequence only by nucleotide substitutions which do not lead to the modification of the amino acid sequence of the above-mentioned polypeptide under conditions likely to cause it to lose the above-mentioned properties.

As an example, the invention relates more particularly to any nucleic acid comprising one or other of the above-mentioned homologous regions of the ACE.

Among the nucleic acids in conformity with the invention, mention should be made in particular of any DNA fragment containing:

a DNA sequence extending from, on the one hand, a nucleotide located between the positions 1 to 1177 to, on the other, a nucleotide located between the positions 3070 and 3940;

a DNA sequence extending from, on the one hand, a nucleotide located between the positions 110 and 1177 to, on the other, a nucleotide situated between the positions 1276 and 1966;

a DNA sequence extending from, on the one hand, a nucleotide located between the positions 1967 and 2971 to, on the other, a nucleotide located between the positions 3070 and 3940.

The invention also relates to the nucleic acids, the nucleotide sequences of which are modified within the limits allowed by the degeneracy of the genetic code, provided that the polypeptides encoded by these nucleic acids conserve either an identical primary structure or their enzymatic or immunological properties.

Such non-limiting modifications lead, for example, to nucleic acid variants which differ from the above nucleic acids:

by addition and/or suppression of one or more nucleotides and/or modification of one or more nucleotides.

The subject of the invention is more particularly any nucleic acid exhibiting the property of hybridizing specifically with the nucleic acid represented in FIG. 3 under the conditions defined below:

prehybridization treatment of the support (nitrocellulose filter or nylon membrane), to which is bound the nucleic acid capable of hybridizing with that of FIG. 3, at 65° C. for 6 hours with a solution having the following composition: 4× SSC, 10× Denhardt, replacement of the pre-hybridization solution in contact with the support by a buffer solution having the following composition: 4× SSC, 1× Denhardt, 25 mM NaPO$_4$, pH 7, 2 mM EDTA, 0.5% SDS, 100 μg/ml of sonicated salmon sperm DNA containing the nucleic acid of FIG. 3 as probe, in particular as radioactive probe, and previously denatured by a treatment at 100° C. for 3 minutes.

incubation for 12 hours at 65° C., successive washings with the following solutions:

four washings with 2× SSC, 1× Denhardt, 0.5% SDS for 45 minutes at 65° C., two washings with 0.2× SSC, 0.1× SSC for 45 minutes at 65° C., 0.1× SSC, 0.1% SDS for 45 minutes at 65° C.

It is to be recalled that the composition of the Denhardt solution is the following: 1% Ficoll, 1% polyvinylpyrrolidone, 1% BSA (bovine serum albumin), and that 1× SSC consists of 0.15M of NaCl and 0.015M of sodium citrate, pH 7.

The invention also relates to any nucleic acid exhibiting the property of hybridizing specifically with the nucleic acid of FIG. 3 under non-stringent conditions which bring into operation the essential features of the stringent conditions defined above except the temperature, which is 40° C. under non-stringent conditions, and the successive washings, which under non-stringent conditions are performed twice with the aid of 2× SSC at 45° C. for 15 minutes.

The invention also relates to nucleotide probes capable of hybridizing with the nucleic acids previously described, or with their complementary sequences, as well as with the messenger RNA coding for the ACE and with the human gene responsible for the expression of the ACE under the hybridization conditions defined above.

It will be obvious that the stringent or non-stringent conditions of hybridization defined above constitute preferred conditions for the hybridization, but are in no way limiting and may be modified without in any way affecting the properties of recognition and hybridization of the probes and nucleic acids mentioned above.

The salt conditions and temperature during the hybridization and the washing of the membranes can be modified in the sense of a greater or lesser stringency without the detection of the hybridization being affected. For example, it is possible to add formamide in order to lower the temperature during hybridization.

The invention also relates to the polypeptide, the amino acid sequence of which is shown in FIG. 3, as well as all of the polypeptides likely to possess an enzymatic activity of the ACE type and which are encoded in the above-mentioned DNA fragments derived from the nucleic acid of FIG. 3.

Among the above-mentioned polypeptides, the following should be singled out:

the polypeptide extending between the amino acids corresponding to the positions 1 and 619 of FIG. 3;

the polypeptide extending between the amino acids corresponding to the positions 620 and 1229;

the polypeptide extending between the amino acids corresponding to the positions 350 and 395;

the polypeptide extending between the amino acids corresponding to the positions 948 and 993.

The polypeptides just mentioned can be modified provided that they conserve the biochemical or immunological or pharmacological properties defined previously.

For example, and in a non-limiting manner, polypeptides within the framework of the invention may differ from the polypeptides defined above;

by addition and/or suppression of one or more amino acids and/or modification of one or more amino acids, provided that the biochemical or immunological or pharmacological properties as defined above are conserved.

It may be taken for granted that the person skilled in the art will have the means to identify, and even select, those polypeptides with shorter sequences which enter into the framework of the invention. As an example of one of the general means which enable him to carry out this identification, mention should be made, for example, of the treatment of the polypeptide of FIG. 3 with a protease which cleaves the above-mentioned polypeptide at a selected site, either in the N-terminal region or in the C-terminal region, followed by the separation of the N-terminal fragment or the C-terminal fragment from the remainder of the said polypeptide, this "remainder" being then tested for its enzymatic activity towards angiotensin and/or bradykinin. In the case of a positive response, it will then have been established that the N-terminal or C-terminal fragment plays neither a significant nor essential role in the expression of the enzymatic properties of the said polypeptide. If required, the operation may be repeated provided that one has available a protease capable of recognizing another specific site close to the N-terminus or C-terminus of the polypeptide remaining. The loss by the shorter polypeptide of the enzymatic properties recognized in the longer fragment from which it was derived may lead to the hypothesis that the fragment which was separated plays a significant role in the expression of the enzymatic properties of the polypeptide of FIG. 3.

Another variant, simpler than the one just mentioned, for the detection of the regions of the ACE essential to the expression of the enzymatic properties of this latter may be based on enzymatic treatment of a nucleic acid coding for the ACE and presumed to code for a polypeptide possessing enzymatic activities of the ACE type before the incorporation of the nucleic acid thus obtained into the expression vector utilized for the implementation of a procedure for the production of the said polypeptide in a suitable cell host (a procedure which will be described in more detail in what follows). This enzymatic treatment may then consist of a trimming of the ends of the original acid (coding, for example, for the entire polypeptide of FIG. 3), for example, by means of an exonuclease enzyme such as Bal31, or by means of one or more restriction enzymes selected for their respective recognition sites (modified, if necessary, by site-specific mutagenesis) in the sequence of the original nucleic acid, or by the addition of a fragment of synthetic DNA linking the cleavage site of the restriction enzyme to the start of the region to be expressed. After incorporation into the selected vector and transformation of the cell host with the recombinant vector obtained, the truncated nucleic acid obtained can then be tested for its capacity to express a corresponding truncated polypeptide still possessing the above-mentioned enzymatic properties-or, on the contrary, no longer possessing them, as a consequence of which, as in the former variant, it is possible to identify within the polypeptide of FIG. 3 the sequences which play an important, if not essential, role in the expression of the enzymatic properties of the ACE.

Another subject of the invention is any recombinant nucleic acid containing any DNA fragment of the type mentioned above coding for the human pre-ACE, or mature human ACE or even for any polypeptide likely to possess an enzymatic activity of the ACE type, linked to a promoter and/or a terminator of transcription recognized by the polymerases of the host cell into which the said recombinant nucleic acid is likely to be introduced.

The introduction of the said recombinant nucleic acid into the cell host is advantageously performed with the aid of vectors, in particular of the plasmid type, which are capable of replicating in the said cell host and of giving rise in it to the expression of the sequence coding for the enzyme.

The said recombinant nucleic acid can also be introduced into the cell host with the aid of a viral vector (recombinant virus) capable of infecting the said cell host and of giving rise in it to the expression of the polypeptide encoded by a nucleic acid according to the invention, this latter being under the control of a viral promoter active in the cell host.

Hence, the invention relates to a procedure for the production of the human ACE or the above-mentioned polypeptides derived from the ACE which comprises the transformation of the host cells by means of the above-mentioned vectors, the placing in culture of the transformed host cells in a suitable medium and the recovery of the said polypeptides either directly from the culture medium, when these latter are secreted into it (particularly in the case in which the polypeptides under consideration are preceded by a signal sequence at the time of their synthesis in the host cell), or after lysis of the wall of the cell host in the case in which the polypeptides are not secreted outside of the host.

The above-mentioned procedure advantageously comprises a final purification step according to the methods of hydrophobic and affinity chromatography, for example, by making use of an inhibitor of all or part of the ACE bound to the column (cf. detailed description which follows).

Therefore, the subject of the invention is more particularly a composition containing the pure human ACE, devoid of contaminants, especially those which are protein in nature.

The host cells used for the implementation of the above-mentioned procedure can be procaryotic cells, in particular *E. coli* cells, or more advantageously, eucaryotic cells which make it possible, in particular, to obtain proteins in their mature and glycosylated form (yeasts, CHO cells, or insect cells infected with baculovirus).

The procedure described above can also be carried out by transfection of the host cells with expression vectors which have integrated a modified gene for the ACE. Either it consists of truncated parts of the DNA complementary to the endothelial messenger RNA for the ACE, comprising for example only one of the two homologous domains, or else cut off from the 3' end coding for the hydrophobic segment for membrane insertion. The transfection of the host cells can also be carried out with vectors containing a mutated form of the ACE or its fragments, the mutations affecting in particular the bases coding for the amino acids described above and implicated in the enzymatic activity.

From the point of view of crystallizing the recombinant enzyme, it is particularly advantageous to mutate one or more potential sites of N-glycosylation, i.e. the codons corresponding to the asparagines in the sequences aspar-agine-X-threonine and asparagine-X-serine in FIG. 3 (X representing any amino acid included between an asparagine and a threonine or a serine in FIG. 3).

The invention also relates to a procedure for the preparation of the novel peptides mentioned above by synthesis which comprises either the stepwise addition of the selected amino acid residues one at the time, with the addition or removal of whatever groups are used for the protection of the amino and carboxyl functions, or the addition of selected amino acid residues in order to produce fragments, followed by condensation of the said fragments to form a suitable sequence of amino acids, with the addition or removal of the selected protecting groups.

The invention also relates to specific antibodies directed against the above polypeptides. In particular, the invention relates to monoclonal antibodies directed against the peptide sequences which appear to be implicated in at least one of the enzymatic activities of the ACE.

Such monoclonal antibodies can be produced by the hybridoma technique, the general principle of which is stated below.

One of the above polypeptides is first inoculated into a selected animal whose B lymphocytes are then capable of producing antibodies against this polypeptide. These antibody-producing lymphocytes are then fused with "immortal" myeloma cells in order to give rise to hybridomas. Starting from the heterogeneous mixture of cells thus obtained, a selection is then made of the cells capable of producing a particular antibody and of multiplying indefinitely. Each hybridoma is multiplied in the form of a clone, each leading to the production of a monoclonal antibody, the properties of recognition of which with respect to the polypeptides of the invention can be tested on an affinity column, for example.

Among the polypeptides utilized for the production of the above-mentioned monoclonal antibodies, mention should be made in particular of those defined by the amino acids located at the positions 350 and 395, or 948 and 993 of FIG. 3.

The invention also relates to an in vitro screening or assay method for a ACE, and more particularly for the human ACE, or for a product derived from the ACE such as the above-mentioned polypeptides which have in vivo the properties of the ACE, in a biological sample likely to contain them. Such a screening method according to the invention can be set up either with the aid of the above-mentioned monoclonal antibodies or with the aid of the nucleotide probes described above.

The above-mentioned biological sample is taken from fluids such as the blood or from organs, this latter type of sample making it possible to prepare fine slices of tissue to which the above-mentioned antibodies can subsequently be bound.

The assay method according to the invention, carried out through the intermediary of the above-mentioned antibodies, comprises in particular the following steps:

the placing in contact of an antibody recognizing the ACE or a polypeptide derived from the ACE according to the invention specifically with the above-mentioned biological sample under conditions leading to the possible production of an immunological complex formed between the ACE or the product which is derived from it and the above-mentioned antibody;

the detection of the above-mentioned immunological complex with the aid of any appropriate agent.

Advantageously, the antibodies used for the implementation of such a procedure are labelled, in particular enzymatically or radio-actively.

Such a method according to the invention can in particular be carried out according to the ELISA (enzyme linked sorbent assay) method, which comprises the following steps:

binding of a predetermined quantity of antibody to a solid support, in particular to the surface of a well of a microplate;

addition of the biological sample (in liquid form) to the said support;

incubation for a time sufficient to allow the immunological reaction between the said antibodies and the ACE or the above-mentioned product which is derived from it;

removal of the unbound parts of the biological sample and washing of the solid support (in particular the wells of the microplate);

addition of an immunoglobulin labelled by an enzyme capable of activating a specific substrate of the enzyme, addition of the substrate specific for the enzymatic activity released during the preceding immunological reaction;

detection of the degradation of the substrate by the enzyme by any appropriate means; and correlation of the amount of enzymes liberated with the concentration of human ACE originally present in the biological sample.

According to another embodiment of the assay method of the invention, the above-mentioned antibodies are not labelled and the detection of the immunological complexes formed between the polypeptides and the said antibodies is achieved with the aid of a labelled immunoglobulin recognizing the said complexes.

The assay method according to the invention can also be carried out by an immunoenzymatic technique depending on a competition mechanism between the polypeptides likely to be contained in the biological sample and predetermined amounts of these same polypeptides for the above-mentioned antibodies. In this latter case, a predetermined quantity of the polypeptides of the invention is advantageously labelled with the aid of an enzymatic marker.

The invention is in no way limited to the embodiments described above for the in vitro assay of the polypeptides of the invention, since this assay can be carried out with the aid of any other suitable immunological method.

The invention also relates to an in vitro screening or assay method for a nucleic acid coding for all or part of the ACE, performed on a biological sample likely to contain the said nucleic acid and characterized in that it comprises:

the placing in contact of a nucleotide probe described above with the above-mentioned biological sample under conditions leading to the possible production of a hybridization complex formed between the nucleic acid and the said probe;

the detection of the above-mentioned hybridization complex with the aid of any suitable agent.

According to an embodiment of the invention, the above-mentioned biological sample is treated, prior to the screening, in a manner such that the cells which it contains are lysed and, where appropriate, in that the genomic material contained in the said cells is fragmented with the aid of restriction enzymes of the type EcoRI, BamHI etc. . . . , or in that the RNAs are isolated from it.

Advantageously, the nucleotide probes of the invention are labelled with the aid of a radio-active or enzymatic marker. The DNAs or RNAs, derived from the biological sample are placed on a suitable support., in particular on a nitrocellulose filter or other support such as a nylon membrane, to which are then added the above-mentioned probes.

According to another advantageous embodiment of the above-mentioned procedure of the invention, histological slices are prepared from the above-mentioned biological sample and the nucleotide probes of the invention are placed in direct contact with the histological slices for the detection of the nucleic acids of the invention by in situ hybridization.

Another subject of the invention is the use of the above-mentioned screening or assay methods for the in vitro diagnosis of diseases such as hypertension, sarcoidosis and other granulomatous diseases, thyroid dysfunctions and, generally speaking, all diseases correlated with concentrations in the organism (in the plasma or other tissues) of the amino acid sequences of the invention which exceed the range defined by the extreme values usually corresponding to the physiological state of a healthy individual.

The in vitro assay method of the invention carried out with the aid of the above-mentioned antibodies also enable the concentration of the inhibitors of the ACE in the organism to be monitored by measurement of the amount of antibody not being able to bind to the active site(s) of the ACE which are masked by the inhibitor. The assay methods of the invention are thus particularly advantageous in the context of the surveillance of patients receiving treatment with inhibitors of the ACE.

Another subject of the invention is kits for the implementation of the above-mentioned in vitro screening or assay methods.

As an example, such kits include in particular:

a defined quantity of one of the above-mentioned monoclonal antibodies capable of giving rise to a specific immunological reaction with the ACE or with one of the polypeptides derived from the ACE according to the invention;

and/or a defined quantity of ACE or a polypeptide capable of giving rise to an immunological reaction with the above-mentioned antibodies;

advantageously, a medium suitable for the formation of an immunological reaction between the ACE or the polypeptides of the invention and the above-mentioned antibodies;

advantageously, reagents making possible the detection of the immunological complexes produced during the above-mentioned immunological reaction.

In the context of the implementation of an in vitro screening method using nucleotide probes, the kits used contain for example:

a defined quantity of one of the above-mentioned nucleotide probes capable of giving rise to a hybridization reaction with one of the above-mentioned nucleic acids coding for the ACE or a polypeptide derived from the ACE according to the invention;

advantageously, reagents leading to the detection of hybridization complexes produced during the above-mentioned hybridization reaction.

The invention also relates to the utilization of the polypeptide of FIG. 3 or any suitable peptide fragment derived from this latter for the design of new inhibitors of the human ACE, more powerful and/or specific towards this latter than are the current inhibitors of the ACE.

Another subject of the invention is a method for the detection or assay of an inhibitor of the ACE or for the quantitation of its inhibitory potency which comprises the placing in contact of the polypeptide of FIG. 3 or any peptide fragment derived from this latter and possessing an enzymatic activity of the ACE type, with the said inhibitor, and the determination of the inhibition coefficient of the enzyme by the inhibitor, in particular by measurement of the possible residual enzymatic activity towards a suitable substrate of the ACE.

The invention also relates to the utilization of the polypeptide of FIG. 3, or of any fragment of this latter capable of hydrolysing the kinins, in particular bradykinin, in the treatment of inflammatory or infectious diseases, acute pancreatitis, and more generally, diseases in which the release of kinins into the organism may play a pathogenic role.

Therefore, the invention relates more particularly to pharmaceutical compositions for the treatment of the diseases indicated above, characterized by the combination of all or part of the polypeptide of FIG. 3, which is capable of hydrolysing the kinins, in particular bradykinin, with a pharmaceutically acceptable vehicle.

Another subject of the present invention is the utilization of the nucleotide probes of the invention, which are capable of hybridizing with the gene responsible for the expression of the human ACE under the conditions described above, for the determination of the different allelic forms of the above-mentioned gene.

Arterial hypertension (AH) is classed into two large categories depending on its etiology: secondary AH and essential AH. Secondary AH brings together all of the forms of AH which medical experience can unequivocally attribute to or associate with an identified disease. It may be, in particular, a hormonal hypersecretion of tumoral (renin or aldosterone, catecholamines, for example) or vascular (stenosis of a renal artery causing a hypersecretion of renin) origin. These secondary forms of AH represent about 5% of all forms of AH. Under the term essential AH are brought together all of the forms of AH for which no etiology can at present be identified and which make up the remaining 95% of all forms of AH.

The pathogenesis of essential AH is presently unknown but many studies have shown that genetic factors are implicated in the development of AH. Studies of families have shown that there exists a familial convergence of the values of arterial blood pressure and that a correlation exists between the arterial blood pressure of the parents and of natural children whereas this correlation does not exist with adopted children. These studies conducted on mono- or dizygotic twins have also confirmed the heriditability of the level of arterial blood pressure. Finally, the genetic analysis of the transmission of the level of arterial blood pressure in man and in genetically hypertensive strains of rats has shown that several genes are implicated. The transmission of this character which is the level of arterial blood pressure and which varies between individuals, thus occurs by the transmission of allelic forms of the genes between parents and children. The genes which may be designated "candidates" for the responsibility of this transmission are, in the first place, those implicated in the principal systems of regulation of arterial blood pressure, such as the genes of the renin-angiotensin system, including the one which codes for the ACE.

The method of choice today for recognizing the allelic forms of a gene is to identify for this gene the size polymorphism of the restriction fragments of this gene (by size of the restriction fragments is meant the number of base pairs which the said fragments comprise). For this type of experiment, the DNAs of several individuals are isolated, cleaved by a restriction enzyme, transferred to a membrane capable of binding them irreversibly and hybridized with a labelled DNA probe corresponding to the gene under study.

This method makes it possible to distinguish the allelic forms of one and the same gene which differ between themselves from one individual to another:

by their restriction map, and/or by the presence of one of the allelic forms of an insertion (an additional DNA fragment in the less frequent allele), or a deletion (DNA fragment missing from the less frequent allele), this insertion not existing in the other allelic forms.

In the first case mentioned above (differences based on the restriction map or also polymorphisms at restriction sites), as a result of the effect of digestion by a given restriction enzyme X, the allele possessing in a precisely defined region of the genome a restriction site recognized by this enzyme is cut by the said enzyme, and the allele not possessing such a site in the said region is not cleaved. With the aid of a nucleotide probe capable of hybridizing with the said region, two restriction fragments of different sizes may thus be detected depending on whether the region concerned is cleaved or not. An allelic form corresponds to each of these sizes.

In the second case (presence of an insertion or a deletion), the fragments of the genomic DNA corresponding to the two allelic forms are cleaved by the restriction enzyme X at an identical site. With the aid of a probe such as that defined in the previous paragraph, it is possible to detect two restriction fragments of different sizes. An allelic form corresponds to each of these sizes, the larger one corresponding to the allelic form containing the above-mentioned insertion.

In the two cases just mentioned and each time that restriction fragments of different sizes (or also polymorphic restriction fragments) are detected in a given gene in different individuals as a result of the effect of the action of a restriction enzyme X, this will be referred to as the "X polymorphism" of this gene (for example "EcoRI polymorphism" if the restriction enzyme X is the EcoRI enzyme, or TaqI polymorphism if the restriction enzyme is TaqI).

The study of a X polymorphism in a selected allele in a given population of supposedly healthy individuals makes it possible to discover the existence of this polymorphism in a defined proportion of the individuals of this population. The measurement of this proportion leads to what will be called hereafter the "reference allelic frequency".

If the frequency of a selected allele, measured by the same method within a population of individuals suffering from a specific disease, is different from the reference frequency, it will then be possible to put forward the hypothesis that the allele in question is associated with the said disease.

Similarly, it will be possible to implicate an allele in the development of the disease if there exists a cosegregation between the transmission of the disease in the families affected and informative for polymorphism, and the transmission of the allele makes it possible to implicate this allele in the development of the disease. (a family is said to be informative for polymorphism if the parent affected by the disease is heterozygote for the restriction site which makes it possible to follow the allele responsible for the disease in the descendants).

The present invention relates to polymorphic restriction fragments capable of hybridizing with a nucleotide probe of the invention, particularly under the conditions described above, and which are derived from the cleavage of different allelic forms of the gene coding for the ACE with the aid of specific restriction enzymes.

The invention relates more particularly to the polymorphic restriction fragments capable of hybridizing with a nucleotide probe according to the invention, itself being capable of hybridizing with the 5' end of the nucleic acid of FIG. 3 and which are the following:

the fragments of 5.8 kb and 6 kb corresponding to TaqI polymorphism, the fragments of 8.8 kb and 9 kb corresponding to DraI polymorphism, the fragments of 8.5 kb and 9 kb corresponding to BglII polymorphism, the fragments of 10.6 kb and 11 kb corresponding to KpnI polymorphism, the fragments of 8.4 kb and 8.8 kb corresponding to HindIII polymorphism, the fragments of 4.2 kb and 3.0 kb, on the one hand, and 4 kb and 2.7 kb, on the other, corresponding to BglI polymorphism, the fragments of 5.2 kb and 5.7 kb corresponding to RsaI polymorphism (in the presence or absence of a fragment of 3.0 kb), the fragments of 4.3 kb, on the one hand, and 2.2 and 2.5 kb, on the other, corresponding to PvuII polymorphism, the fragments of 3.5 kb and 3 kb corresponding to XbaI polymorphism, the fragments of 4.3 kb and 2.7 kb corresponding to TaqI polymorphism.

The difference in size of the allelic fragments recognized by the probes of the invention in different individuals corresponds to an insertion of a genomic fragment of about 400 base pairs with a margin of error due to the analysis of the size of these fragments by electrophoresis on agarose gel.

This insertion can be detected with the aid of any restriction enzyme cleaving the above-mentioned nucleic acid at the time when the fragments created are capable of hybridizing, at least in part, with the corresponding probe.

The present invention relates to an in vitro screening procedure for the polymorphisms of the gene coding for the expression of the human ACE, carried out on biological samples such as blood which are likely to contain the genomic DNA and which are taken from a given population of individuals not suffering from AH (or also normotensive individuals), or other diseases of the vascular endothelium.

The above-mentioned samples are analysed according to the following method comprising:

the treatment of the nucleic acids derived from the above-mentioned biological samples with the aid of a specific restriction enzyme under conditions leading to the formation of restriction fragments derived from the cleavage of the said nucleic acids at the restriction sites recognized by the said enzyme, the placing in contact of a nucleotide probe according to the invention capable of hybridizing with the above-mentioned fragments under conditions leading to the possible production of hybridization complexes between the said probe and the above-mentioned restriction fragments, particularly under the hybridization conditions defined above, the detection of the above-mentioned hybridization complexes, the measurement of the size of any polymorphic restriction fragments involved in the above-mentioned hybridization complexes.

Among the probes used for the implementation of such a procedure, mention should be made in particular of the DNA (or cDNA) complementary to the nucleic acid described in FIG. 3 or, advantageously, a fraction of this cDNA capable of hybridizing with different restriction fragments corresponding to the different allelic forms of the gene of the ACE.

Advantageously, the probe used in the above-mentioned procedure is labelled, in particular radio-actively or non-radioactively, in the form of a biotinylated probe in order to make possible the detection of the different restriction fragments remaining hybridized with the said probe.

The measurement of the size of the different polymorphic restriction fragments involved in hybridization complexes with the above-mentioned probe may be carried out by any method known to the person skilled in the art; the determination of the size of these restriction fragments is carried out in particular by electrophoresis on agarose gel and estimation of the size of the said fragments in comparison with those of reference fragments.

The comparison of the sizes of the restriction fragments measured in the individuals of the population under study makes it possible to establish the reference allelic frequencies within this population of individuals.

The invention also relates to the detection of the different allelic forms of the gene coding for the human ACE which are likely to be associated with the development of a AH or other diseases of the vascular endothelium, in particular atherosclerosis in an individual. This detection is performed according to the same method within a population of individuals suffering from one of the above-mentioned diseases. If the frequency of an allele measured within this population is different from the reference frequency, it will then be possible to put forward the hypothesis that this allele is probably linked to the AH.

Similarly, it will be possible to implicate an allele in the development of the disease if there exists, in the families affected by the disease and informative for the polymorphism, a cosegregation of the transmission of certain allelic forms of the gene for the ACE with the transmission of the AH and/or diseases of the endothelium, in particular atherosclerosis.

Another subject of the invention is the use of the results of the study of the polymorphisms of the gene coding for the human ACE for the in vitro diagnosis of any genetic predisposition which is probable in an individual with arterial hypertension or with other diseases of the vascular endothelium, in particular atherosclerosis.

The in vitro diagnostic method mentioned above comprises the posssible detection of polymorphic restriction fragments derived from the cleavage by a specific restriction enzyme of alleles probably associated with the mechanism of the AH, with the aid of nucleotide probes according to the invention, which are capable of hybridizing with the said polymorphic restriction fragments.

The conditions under which such an in vitro diagnostic method can be implemented are those described in the articles concerning the techniques for the detection of the polymorphisms in the length of the restriction fragments, still better known under the abbreviation RFLP (Restriction Fragment-length Polymorphism). Such conditions are more particularly described in the article by GUSELLA J. F. "Recombinant DNA techniques in the diagnosis of inherited disorders" published in *Journal of Clinical Investigations* (1986), 77, 1723–1726.

According to an attractive feature of the invention, in addition to the screening of the polymorphisms of the gene coding for the human ACE, the above-mentioned in vitro diagnostic method also comprises the screening of polymorphisms of one or more genes coding for proteins different from the ACE and implicated in the regulatory mechanism of arterial blood pressure.

Therefore, the in-vitro diagnostic method according to the invention comprises the screening of polymorphisms of the gene for the ACE, the gene for renin, and/or the gene for kallikrein, and/or the gene for the ANF.

Among the above-mentioned polymorphisms of the genes coding for renin, kallikrein and the ANF, mention should be made in particular of those which were described more particularly in the PCT patent application published under the number WO87/02709 filed on 23 Oct. 1987.

With the aid of suitable probes, the authors of that PCT application discovered the following restriction fragments:

5 kb and 9 kb corresponding to BglII polymorphism of the renin gene, 0.9 kb corresponding to BglII polymorphism of the renin gene, 20 kb and 24 kb corresponding to RsaI polymorphism of the renin gene, 6.2 kb and 9 kb corresponding to HindIII polymorphism of the renin gene, 9.8 kb and 11 kb corresponding to TaqI polymorphism of the renin gene, 3.9 kb corresponding to EcoRI polymorphism of the renin gene, 1.4 kb and 1.8 kb corresponding to BamII-polymorphism of the ANF gene, 4.1 and 6.2 kb corresponding to BglI polymorphism of the ANF gene, 9.1 kb and 6.5 kb corresponding to BglII polymorphism of the ANF gene, 5.2 kb and 11.8 kb corresponding to the EcoRI polymorphism of the ANF gene, 15 kb corresponding to the EcoRI polymorphism of the kallikrein gene, 3.1 kb corresponding to PstI polymorphism of the kallikrein gene, 4.5 kb corresponding to StuI polymorphism of the kallikrein gene.

Another subject of the invention is kits for the implementation of the in vitro diagnostic method defined above.

As an example, such diagnostic kits contain:

a defined quantity of one or more restriction enzymes, a defined quantity of a nucleotide probe capable of recognizing the restriction fragments derived from the cleavage of the gene coding for the ACE by the above-mentioned enzyme(s), possibly a defined quantity of a probe capable of recognizing the restriction fragments derived from the cleavage of the gene coding for renin by the above-mentioned enzyme(s), and/or a defined quantity of a probe capable of recognizing the fragments derived from the cleavage of the gene coding for kallikrein by the above-mentioned enzyme(s), and/or a defined quantity of a probe capable of recognizing the restriction fragments derived from the cleavage of the gene coding for the ANF by the above-mentioned enzyme(s).

The standard techniques of gene amplification, in particular that described in the U.S. Pat. No. 4,683,202 filed on Oct. 25, 1985 can be used to detect the polymorphism of the gene coding for the ACE by using primers which hybridize with this gene on either side of the insertion of about 400 base pairs mentioned above. The DNA fragments thus amplified have a size difference depending on whether or not the genomic DNA fragment contains the said insertion.

In this respect, the subject of the invention is more particularly any nucleotide sequence of about 10 to 40 nucleotides derived from the nucleotide sequence of FIG. 3, or from its complementary sequence, or likely to hybridize with a part of the sequence of FIG. 3 or with the sequence complementary to the latter, which can be used as primers for the amplification of the gene coding for the ACE.

Additional characteristics of the invention will also become apparent during the course of the description which follows of the cloning of the nucleic acid coding for the human ACE as well as of the clones used for this cloning, it being understood that this description is not to be interpreted as tending to limit the scope of the claims.

I—PURIFICATION AND SEQUENCING OF THE ACE

The human ACE in its complete membrane form was purified from renal microsomes. The microsomal fraction was prepared from homogenates of kidneys of human cadavers in the following manner: 600 g of renal cortex were minced, suspended in 20 mM potassium phosphate buffer, pH 8, containing 250 mM of sucrose and a mixture of protease inhibitors (5 mM sodium tetrathionate, 10 mM N-ethylmaleimide, 2 mM phenylmethanesulfonyl fluoride), and homogenized for 3 minutes. The tissue debris were removed by centrifugation at 5000 g for 20 minutes and the particulate fraction was sedimented by centrifugation at 105,000 g for 1 hour. The pellet was resuspended in 150 mM potassium phosphate buffer, pH 8 (buffer I, 200 ml) and treated for 18 hours with the detergent 8 mM CHAPS (Serva). After centrifugation at 105,000 g for 1 hour, the supernatant was dialysed against buffer I for 24 hours in order to remove the CHAPS. Then it was loaded onto a column of phenyl-Sepharose 4B (Pharmacia) and eluted at a rate of 24 ml/hour; 60% of the enzymatic activity was retained on the column and eluted in the form of a single peak after application of a linear gradient of CHAPS (3-(3-cholamidopropyl)-dimethylammonio- 1-propanesulfonate)up to a concentration of 10 mM (800 ml). The eluate was enriched with $ZnSO_4$ and KCl to final concentrations of 0.1 mM and 330 mM, respectively, so as to obtain optimal binding with the inhibitor, then the purification was completed on a column of lysinopril-Sepharose 4B as described in BULL, H. G. et al, (1985), *J. Biol. Chem.*, 260, 2963–2972.

After reduction (5% 2-mercaptoethanol) and denaturation (boiling for 3 minutes), the protein thus isolated (1.2 mg) was analysed by means of electrophoresis on a 6% polyacrylamide gel containing $NaDodSO_4$ (LAEMMLI, U. A., (1970), *Nature*, 227, 680–685).

The purified enzyme hydrolyses angiotensin I, bradykinin and several synthetic substrates, and is inhibited by captopril and other inhibitors of the ACE. The determination of the enzymatic activity was performed with the aid of the substrate furanacryloyl-L-phenylalanyl-glycyl-glycine (FAPGG) under the conditions described in HOLMQUIST et al (1979), *Anal. Biochem.*, 95, 540–548. The parameters of the enzymatic reaction determined at pH 7.5 are 136 μm for $K_m$ and 22100 $min^{-1}$ for Kcat; a treatment with cyanogen bromide was used to cleave the enzyme at the methionine residues, thus generating fragments for sequencing. The purified ACE (0.5 mg) was dissolved in 70% formic acid (0.2 ml) and cyanogen bromide (2.0 mg) was added. After 16 hours of reaction at room temperature in the dark, the solution was diluted 20 fold with water and lyophilized.

The peptide fragments were isolated by reverse phase HPLC by using a gradient system consisting of trifluoroacetic acid (TFA)-water-acetonitrile (buffer A: 0.1M of TFA in water; buffer B: 0.1% of TFA in acetonitrile; 1–100% of B in 32 minutes, elution rate 1 $ml.min.^{31}$ $^1$). The fractions corresponding to the various peaks were separated and lyophilized, and sequenced with the aid of an automatic sequencer. The peptide fragments thus obtained are presented in FIG. 1A. The amino-terminal sequence of the protein was determined by the Edman method with the aid of an automatic sequencer using the whole ACE protein.

The following sequence of 16 amino acids was obtained $NH_2$ — Leu — Asp — Pro — Gly — Leu — Gln — Pro — Gly —

— Asp — Phe — Ser — Ala — Asp — Glu — Ala — Gly — COOH

II—CLONING OF THE DNA COMPLEMENTARY TO THE MESSENGER RNA

A) Nucleotide probe starting from the peptide sequence Met-Trp-Ala-Met-Trp-Ala-Gln-Ser-Trp-Glu-Asn-Ile (based on the CN8b sequence of FIG. 1A), 64 nucleotide probes designated HACE6 were synthesized with the aid of an automatic DNA synthesizer using the phosphoramidite method.

Met — Trp — Ala — Lys — Ser — Trp — Glu — Asp — Ile — 3'

TAC—ACC—CGA—TTT—ACG—ACC—CTT—TTG—TA 5'
    G      G TG         C    A

Radioactive labelling: the probe HACE6 was labelled with [$\alpha$-$P^{32}$] ATP (specific activity: 5000 curies/mmole) at its 5' end by the T4 polynucleotide kinase. The specific activity of the probe is $5 \times 10^6$ cpm/pmole.

B) Screening of a bank of complementary. DNAs constructed from the RNA of endothelial cells A cDNA bank of endothelial cells of the human umbilical vein primed with oligo(dT), constructed in the phage λgt11 (Clontech Laboratories Inc.) and constituted of $1.5 \times 10^6$ independent recombinants) was screened by using the probe HACE6 labelled with $P^{32}$. The DNA of the phages was transferred to a nitrocellulose filter according to the method of Benton and Davis (ref. BENTON, W. D. and DAVIS R. W. (1977), *Science* (Wash), 19.6, 180–182). The hybridizations with HACE6 were performed in: 6× SSC, 0.1% of NaDodSO$_4$, 50 mM NaPO$_4$ buffer at pH 6.8, 5× Denhardt, 0.1 mg/ml of denatured salmon sperm DNA at 50° C. The final washing of the filters was done twice with 2× SSC, 0.1% SDS at 55° C. for 15 minutes.

Under these conditions two different types of clones hybridizing strongly with the probe HACE6 were obtained. They are the clones λHEC1922 and λHEC2111. The DNA fragments inserted into the phages were isolated after cleavage of the phages by the restriction enzyme EcoRI, and inserted in both senses into the bluescript plasmid (Stratagene), at the EcoRI site of this latter. Starting from these double-stranded plasmids, mono-stranded matrices were obtained by reinfecting bacterial cultures carrying these plasmids with the aid of a helper phage K07.

The determination of the nucleotide sequence of these clones was carried out by the method of Sanger (SANGER, F. et al (1977), *Proc. Natl. Acad. Sci.*, USA, 74, 5463–5467) by using either the Klenow DNA polymerase or the modified DNA polymerase of T7 (Sequenase, US Biochemical). Some regions were sequenced by using deoxyinosine triphosphate (dITP) or deaza-deoxyguanosine triphospate (7-deaza dGTP) instead of deoxyguanosine triphosphate (dGTP). The electrophoresis of the fragments labelled with S$^{35}$ dATP was carried out on a ureapolyacrylamide gel. The sequences were established by synthesizing step by step about every 350 base pairs oligomers which served as primers placed at intervals throughout the entire sequence.

The nucleotide sequences inserted into these two phages are overlapping over a length of 2323 base pairs. The peptide sequence deduced from these clones contains all of the peptide sequences obtained by purification of the human ACE and which are shown in FIG. 1A, with the exception of the amino-terminal region.

In order to obtain the complementary DNA corresponding to the 5' end of the messenger RNA coding for the ACE, another cDNA bank was constructed by utilizing 5 µg of poly(A) RNA isolated from endothelial cells of the umbilical vein in tertiary culture. These cells were obtained by dissociation with the aid of collagenase as described in JAFFE et al (JAFFE J. M. et al (1973), *J. Clin. Invest.*, 52, 2745–2756) and were cultivated in the presence of 20% of fetal calf serum, 100 µg/ml of heparin and 2 ng/ml of FGF (fibroblast growth factor) (GOSPORADOWICZ, D. et al (1983) *J. Cell. Biol.*, 97, 1677–1685). The total RNA was extracted from the cells after 3 subcultures by the method of Chirgwin et al (CHIRGWIN, J. M. et al (1979), *Biochemistry*, 18, 5294–5299) and purified on oligo-dT7 cellulose (Pharmacia). The complementary DNA bank was constructed according to the method of Gubler and Hoffman (*Gene* (1983) 25, 263–269) by using as primer a mixture of two oligonucleotides. The first oligonucleotide is a primer specific for the mRNA of the ACE, determined by the sequence of the clones previously obtained. It is an oligomer of 17 bases (CP5-21) complementary to a sequence localized near to the 5' end of the cDNA of the ACE (nucleotides 234 to 250 of FIG. 3). The second primer corresponds to the oligo-dT12-18 mers (Pharmacia). The cDNAs were treated and inserted into the phage gGT10 cleaved by the EcoRI enzyme according to the method of Koenig et al (KOENIG, M. et al (1987), *Cell*, 50, 509–517).

The recombinant phages were screened with the aid of a fragment of 300 base pairs of human genomic DNA isolated from a genomic bank cloned into the phage CHARON4A and which hybridizes with CP5-21, and with the oligonucleotide of 44 bases obtained from the amino-terminal sequence deduced for the purified ACE according to the method described above.

This restriction fragment (SacII-SacII) of 300 base pairs contains the most 5' terminal part of the messenger RNA of the ACE; it was labelled with high specific activity using the labelling method described by FEINBERG A. P. et al (1983), *Anal. Biochem.*, 132, 6–13, and used for screening 1.5×10$^6$ clones under highly stringent conditions.

Of the positive clones obtained, the clone λCHDT32 was selected and sequenced according to the same method as that described for the previous clones. It was thus established that this clone contains an insertion of 246 base pairs and that it starts 7 nucleotides upstream from the primer CP5-21 and that it stops 25 nucleotides upstream from the ATG codon for the initiation of translation.

The insertion in this clone shares 60 base pairs with the clone λHEC2111 and contains the 5' end of the sequence coding for the ACE.

The nucleotide sequence of the cDNA coding for the ACE obtained by sequencing of the previous three clones thus contains 4024 nucleotides. The 3' end of this sequence does not contain the polyadenylation signal.

The open reading frame starting from the first ATG codon up to the stop codon TGA codes for 1306 amino acids. The amino-terminal leucine determined by sequencing of the protein is localized after a signal peptide of 29 residues.

The clone λHEC1922 was used as probe in order to study the expression of the gene coding for the ACE by the method called "Northern Blot" according to the procedure of Thomas et al (THOMAS, P.S. et al (1983) *Methods in Enzymology*, N. Y. Academic Press, 100, 255–266). A messenger RNA of about 4.3 kb from endothelial cells of the umbilical vein in culture hybridizes with the above-mentioned probe. In the testis, only a shorter messenger RNA of 3 kb has been detected. In the kidneys, which are a rich source of ACE, no hybridization was detected under the conditions used using 20 µg of poly(A) RNA, which suggests that the synthesis and the levels of turnover of the ACE are low in this organ.

An analysis by means of "Southern blot" of the human DNA under stringent conditions was carried out with a EcoRI-BglII fragment of 300 base pairs localized at the 5' end of the λHEC2111 clone. The human DNA was isolated from the nuclei of cells of the placenta by treatment with proteinase K followed by extractions with a phenolchloroform mixture. The DNA (14 µg) was digested with HindIII, separated on 0.7% agarose gel and analysed by hybridization according to the "Southern blot" method (SOUTHERN, E. M. (1975) *J. Mol. Biol.*, 98, 503–517).

The DNA fragments were labelled according to the method described in FEINBERG, A. P. et al (1983) *Anal. Biochem.*, 132, 6–13. This probe hybridizes with a unique restriction fragment of 9.5 kb.

Similar results were obtained by using a cDNA fragment close to the 3' end.

This result confirms the presence of a single gene. The determination of the enzymatic activity of the ACE encoded by the gene thus isolated or of any active peptide according to the invention and derived from this latter, can be done in particular by the method described by Holmquist et al (1979) previously cited.

The assay of this human ACE can be carried out by radioimmunological techniques (RIA) described by HIVADA K. et al (1987) *Lung*, 267, 27–35.

III—POLYMORPHISMS OF THE ACE GENE

The DNA from several individuals was isolated from nucleated cells by lysis of the red cells followed by a lysis of the leucocytes, a treatment with proteinase K and by successive extractions with phenol and chloroform followed by precipitation with isopropanol.

A defined quantity of DNA is then digested by a restriction enzyme and allowed to migrate on an agarose gel which separates the DNA fragments as a function of their size. The DNA is then denatured by a treatment with 0.5N sodium hydroxide and transferred to a nylon membrane by blotting for 12 hours. The DNA is then bound to the membrane by being placed in an oven for 2 hours at 80° C.

The membrane is then pre-hybridized with a 4× SSC, 10× Denhardt solution for at least 6 hours at 65° C. The membrane is then hybridized with a 4× SSC, 1× Denhardt, 25 mM NaPO$_4$, pH 7, 2 mM EDTA, 0.5% SDS, 100 µg/ml of sonicated salmon sperm DNA buffer solution containing the labelled probe denatured by heat at 100° C. for 3 minutes.

The labelled probe is a mixture of cDNA fragments of the ACE contained in the clones λHEC1922 and λHEC1922.

The purified DNA fragments are labelled at high specific activity by the statistical primer technique using the Klenow fragment of the *E. coli* polymerase and a deoxynucleotide labelled with P$^{32}$ at high specific activity.

The membranes are hybridized in the presence of the probe for 12 hours at 65° C.

After hybridization, the membrane is washed four times with a 2× SSC, 1× Denhardt, 0.5% SDS solution at 65° C. for 45 minutes, then washed twice with a 0.2× SSC, 0.1× SSC solution for 45 minutes at 65° C., then with a 0.1× SSC, 0.1% SDS for 45 minutes at 65° C.

The sequences having hybridized with the probe are then visualized by autoradiography of the membranes on a film at −80° C. in the presence of an intensifying screen.

The analysis of the DNA of several individuals with the cDNA probes of the ACE or equivalent probes, i.e. shortened at one of the two ends, or elongated towards the 3' or 5' end of the transcribed or non-transcribed part of the gene, or synthetic fragments of DNA which conserve the property of hybridizing with the above-mentioned restriction fragments, makes it possible to distinguish several types of restriction fragments as a function of the enzymatic cleavages of the DNA. These fragments are the following:

5.8 kb or 6 kb by TaqI digestion,
8.8 kb or 9 kb by DraI digestion,
8.5 kb or 9 kb by DglII digestion,
10.6 kb or 11 kb by KpnI digestion,
8.4 kb or 8.8 kb by HindIII digestion,
4.2 kb and 3.0 kb or 4 kb and 2.7 kb by BglI digestion,
5.2 kb or 5.7 kb by RsaI digestion, with the presence or absence of a band at 3.0 kb,
3.5 kb or 3 kb by XbaI digestion,
4.3 kb or 2.7 kb by TaqI digestion.

As a result of digestion with the enzyme PvuII, two restriction patterns or profiles are obtained including or not the presence of a band at 4.2 kb which is associated with a weaker band of 2.2 and 2.5 kb.

We claim:

1. A biologically functional plasmid or viral DNA vector including a DNA sequence encoding human angiotensin converting enzyme.

2. A procaryotic or eucaryotic host cell transformed or transfected with a DNA vector according to claim 1.

3. A method for producing human angiotensin converting enzyme, comprising:

transforming host cells with the vector according to claim 1, placing the transformed host cells in culture medium, and recovering human angiotensin converting enzyme from said host cells or from the culture medium.

* * * * *